United States Patent [19]

Buffa

[11] 4,303,064
[45] Dec. 1, 1981

[54] ORAL HYGIENE DEVICE

[76] Inventor: Michael J. Buffa, 277 Lindenmere Dr., Merrick, N.Y. 11566

[21] Appl. No.: 192,213

[22] Filed: Sep. 30, 1980

Related U.S. Application Data

[63] Continuation of Ser. No. 27,867, Apr. 6, 1979, abandoned.

[51] Int. Cl.³ .............................................. A61H 7/00
[52] U.S. Cl. .................................. 128/62 A; 401/289
[58] Field of Search ....................... 128/229, 66, 62 A; 401/291, 289, 284, 270

[56] References Cited

U.S. PATENT DOCUMENTS

| | | | |
|---|---|---|---|
| 844,256 | 2/1907 | Curcio | 401/270 |
| 1,325,200 | 12/1919 | Kirsch | 401/270 |
| 1,435,558 | 11/1922 | Sencindiver | 128/66 X |
| 1,452,976 | 4/1923 | Lichtenstein | 401/289 X |
| 1,913,079 | 6/1933 | Hegge | 401/289 X |
| 3,618,596 | 11/1971 | Miller | 128/66 |
| 3,618,597 | 11/1971 | Godel | 128/66 |

FOREIGN PATENT DOCUMENTS

| | | | |
|---|---|---|---|
| 154985 | 6/1938 | Austria | 401/291 |
| 434219 | 5/1948 | Italy | 401/291 |

Primary Examiner—John D. Yasko
Attorney, Agent, or Firm—Morgan, Finnegan, Pine, Foley & Lee

[57] ABSTRACT

A combined fluid jet-brush oral hygiene device which provides a means for plaque removal on the buccal, lingual and interproximal surfaces of the teeth as well as gingival stimulation.

3 Claims, 4 Drawing Figures

ORAL HYGIENE DEVICE

This is a continuation, of application Ser. No. 27,867 filed Apr. 6, 1979 now abandoned.

BACKGROUND

(1) Field of Invention

This invention relates to the field of oral hygiene and more particularly to oral hygiene devices and processes which utilize a brushing instrumentality and fluid jet discharge in combination to effect enhanced massaging action, plaque and debris removal.

(2) Summary of Prior Art

The use of brushing means in conjunction with, or apart from, fluid jet means is known to be an important part of an individual's oral hygiene routine. It is also known that the use of brushing means alone provides the user with necessary massaging action in addition to the cleansing action of the brush abrading the surfaces of the teeth. Use of a fluid jet alone has a different beneficial effect, in that it is useful in clearing damaging bacterial products from relatively inaccessible gingival and subgingival areas where bacteria may proliferate and enhance the decay process.

The effectiveness of fluid jet devices alone is still controversial. However, clinical results suggest that such devices produce beneficial results in the mouths of patients with extensive bridgework, splints, or orthodonic bands, especially when used in conjunction with flossing and brushing.

The fluid jet device alone will not remove all plaque. The combination of brush (to dislodge the more tenacious deposits) and fluid jet, is more highly recommended in a plaque control program.

Of all the methods of plaque removal, the toothbrush is the most universally accepted, it is easy to use and is the most socially acceptable mode for cleaning the mouth. Its effectiveness, however, depends greatly upon the frequency of its use. Most persons will benefit from brushing more than one time per day. To promote repetitive use, the device should be simple, otherwise the user may be discouraged.

Brushing alone, however, often will not clean gingival and sub-gingival areas, and bacterial and plaque deposits will remain there, even after brushing. It is therefore beneficial to utilize both brushing means and fluid jet means simultaneously.

The use of both brushing and fluid jet action together has many beneficial effects. The fluid jet, when properly combined with the brushing action, serves to enhance the latter's efficacy and to reduce buildup of undesirable materials, missed by brushing; it also serves to carry the dislodged materials away from dental surfaces by reason of its irrigating properties.

Combined usage also produces a clean feeling in the mouth of the user.

Thus, it has long been an object, of those involved in the field of dental hygiene, to effectively combine brushing means and a fluid jet means, in order to realize the benefits described above.

The earliest attempts to combine the two resulted in devices wherein the brushing means and the fluid jet means were inextricably combined. It was thus impractical to use the fluid jet means apart from the brushing means. This is disadvantageous to the user, as the full advantages of using the fluid jet means alone will not be realized.

Subsequent designs were employed whereby a single fluid jet source could be utilized with two different attachments, one of which would be a brushing means combined with a fluid jet, a second being a solitary fluid jet attachment. This would allow the user to choose which of the two applications (brushing and fluid jet, or fluid jet alone) he desired, by attaching the appropriate outlet. These devices however employed designs which made it difficult for users to switch readily from one application to another.

The consequence of this deficiency may be seen by noting that the most logical and common method of using the fluid jet means is to first employ the brushing means in conjunction with a cleansing agent (e.g., toothpaste), and also in conjunction with the fluid jet means. The combination of these three agents allows the user to first remove all debris from the outer surfaces of the teeth by use of the brushing means, allows brushing means to further massage the gums and provide the salutary effects associated therewith, and simultaneously have the fluid jet action enhance the brushing action and dislodge debris. Following this the user would disengage the brushing means, at this point soiled, and utilize the fluid jet alone. The jet at this time may be utilized to carry away the remains of the cleansing agent and/or any debris which may yet remain on the surface of the teeth, as well as for its primary purpose of cleansing the gingival areas and providing stimulation to those areas. The prior art devices referred to above make it difficult for the user to conveniently follow this procedure, as the prior art devices are clumsy and difficult to implement. The user, in order to follow this procedure would have to employ a cumbersome and relatively time-consuming process, for he would have to first remove entirely the first (brushing) attachment and then engage the second (fluid jet) attachment.

Many of the prior art devices involve the use of screw-on attachments. Thus, the removal of one attachment and the securing of the other takes quite a bit of time. Even utilizing a clamp-on or snap-on technique, however, does not make the process simple or convenient. It is still necessary for the user to interrupt the procedure and disengage the brushing attachment. This pause will often occur while the user has his mouth full of the cleansing agent leaving a bad taste and uncomfortable feeling in the mouth. Furthermore, it is well known that complications tend to discourage the regular use that is essential to effective oral hygiene.

It is thus disadvantageous to minimize the amount of time the user must spend and actions he must take in changing or removing the brushing means.

Another disadvantage is found in those instruments which provide both hydraulic flow action and brushing action, and by the use of a movable connection allow the user to pivot or slide the fluid jet means away from the brushing means, or vice versa. By retaining the brushing means in relatively close proximity to the fluid jet means after this routine is followed, the brushing member is retained close to the face of the user. This is both inconvenient and unsanitary. Furthermore, the use of a movable interconnection may lead to the build up of debris and waste material in moving parts and inner recesses of the instrument, with consequential bacterial proliferation. This too is unsanitary. Furthermore, in certain applications, such as in institutional settings, it is often advantageous to allow the user to completely dispose of the soiled brushing member after use or to sterilize it. These features are not readily attained in the above described arrangements.

Finally these prior art designs are not susceptible to use with commercially available hydraulic flow means. This means that a potential user, who may already have a fluid jet cleaning instrument (such as that currently traded under the name of WATER-PIK) would have to purchase a completely new system. Furthermore, from a manufacturing and marketing standpoint, it is often more advantageous to make and market an adaptation to a popular preexisting device.

It should also be pointed out that the effectiveness of a toothbrush is derived from the stiffness of its bristles. The stiffness will deteriorate in a matter of weeks after continuous usage. An inexpensive brushing device, such as that described herein, will encourage users to dispose of used, ineffective brushes. The user will therefore benefit from an increased effectiveness of his oral hygiene routine.

It is therefore one object of this invention to provide a brush-fluid jet oral hygiene instrument which allows the user to conventionally realize the salutary effects of brushing means alone, brushing combined and enhanced with fluid jet action, and fluid jet action alone.

It is a further object of this invention to provide a combined brush-fluid jet oral hygiene instrument which has simple and convenient means for selecting either brushing alone, brushing with fluid jet action, or fluid jet action alone.

It is a still further object of the device to provide an easily removable brushing member in a brush-fluid jet oral hygiene instrument so that sterilization or "throwaway" use may be readily accomplished.

Another object of the invention is to provide an inexpensive and easily manufactured attachment for a preexisting commercially available fluid jet oral hygiene instrument.

DETAILED DESCRIPTION

Figure 1:
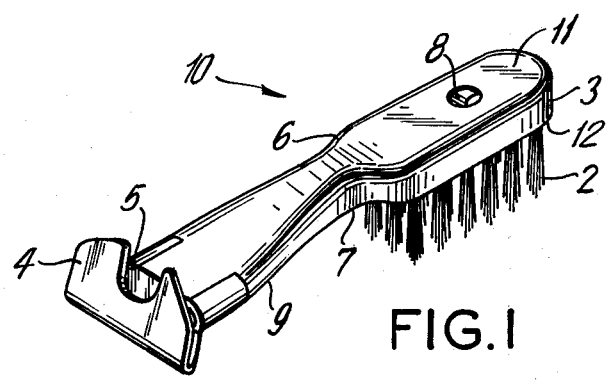
FIG. 1 is a perspective view of the brush component of one embodiment of the invention.
Figure 3:
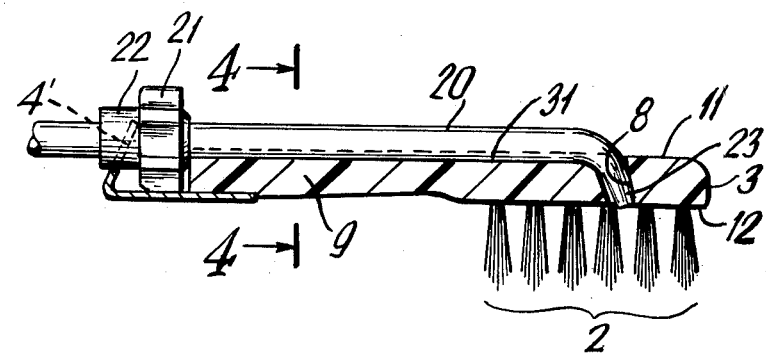
FIG. 3 is an elevational view partly schematic and partly sectional of another embodiment of the invention.

The drawing depicts two preferred embodiments of the brushing means, generally indicated by the reference numeral 10 in FIG. 1, and 30 in FIG. 3.

Brushing means 10 of FIG. 1 includes a generally elongated body member 6 having a brushing member 2 at one end thereof, a flange 4 containing a cutout portion 5 at the opposite end thereof, and fluid conduit 8 in the brushing section. The body member 6 of the device may be made of any suitable material; a plastic such as polypropylene is illustrative. Member 6 is illustratively shaped much as a standard toothbrush, i.e., it has a generally rectangular head 3 on which the brushing member 2 is located, an intermediate tapering neck 7 and a larger shank section 9.

The brushing member 2 of the device is affixed to the underside 12 of the head 3, and is composed of a series of groups of standard bristles preferably in the soft to medium stiffness range arranged in rows and columns, as is done in conventional designs. In the midst of the groups of bristles is the exit port of the fluid conduit 8. (See also, FIG. 2)

The fluid conduit 8 extends through the head 3 from the topside 11 thereof to the underside 12. The exit port of the conduit on underside 12 is located between either the first and second row of bristles or the second and third rows of bristles. Experimentation has shown that superior performance is realized by such positioning. Both the jet action and the scrubbing action appear to be synergistically enhanced.

At the distal end of the trunk 9 is positioned the flange 4. The flange is generally resilient and biased at an acute angle to the shank 9. (The angle referred to being the interior angle between the planes of the flange 4 and shank 9.) The flange 4 is illustratively of a generally semi-circular nature, containing however, a cutout portion 5 shaped to accommodate the fluid jet means 20, now to be described.

Figure 2:
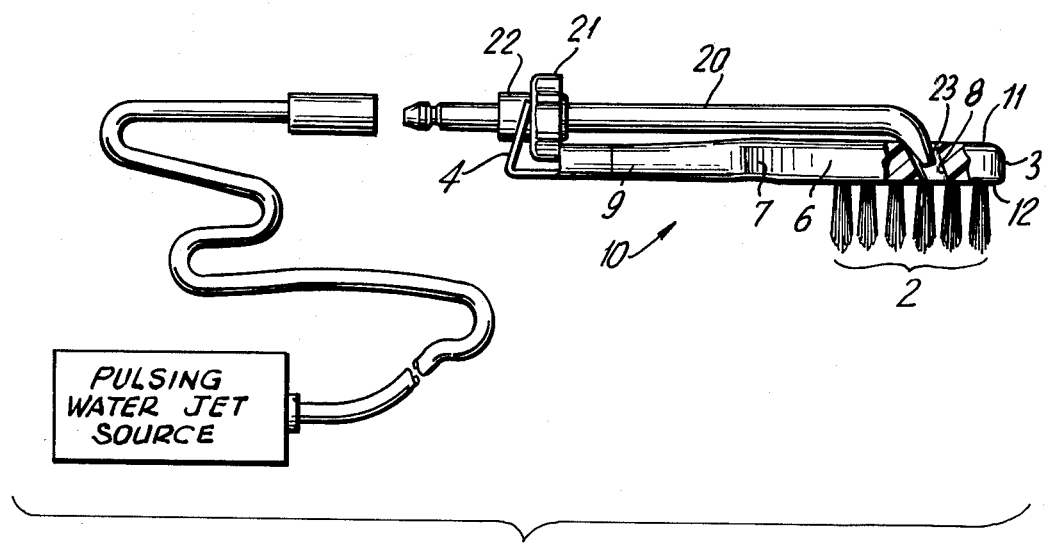
FIG. 2 is an elevational view partly schematic and partly sectional of an embodiment of the invention including the brush component of FIG. 1.

As illustrated in FIG. 2, the fluid jet means 20 is coupled to brushing means 10, and in the preferred embodiment is the discharge tube of the instrument marketed under the trade name WATER-PIK.

The fluid jet means 20 has at one end thereof, a collar 21 and a bushing 22, and at the other end an exit nozzle 23. The exit nozzle is inserted in the entrance port of conduit 8 of the brushing means 10 as illustrated. With fluid jet means 20 clipped to brushing means 10, the flange 4 has been contacted and deflected by the collar 21, causing a resilient pressure to be exerted axially along the fluid means 20 in the direction of the head 3. Inasmuch as the nozzle 23 of the jet flow device is constrained within the conduit 8, the fluid jet means 20 is removably secured to the brush holder 10.

To accomplish this engagement, the user attaches the brushing means 10 to the fluid jet means 20 by placing the exit nozzle 23 of the fluid jet means 20 into place. This "snapping" is effected by collar 21 deflecting flange 4 away from shank 9, and having flange 4 therefore exert pressure on the collar 21, as described above. The "snapping" effect is necessary because hydraulic jet devices are manufactured in different lengths. It is therefore possible to adapt the invention for use with several preexisting commercial devices. Improved engagement is provided by the cutout portion 5 of flange 4 designed to receive bushing 22. With this configuration, the fluid jet means 20 is better secured to the brushing means 10.

Once brushing means 10 and fluid jet means 20 are connected, and the latter is secured to the pulsing fluid jet source (FIG. 2), the system is ready for use. The user may apply a cleansing preparation to the bristles of the brushing member, if desired, to enhance the cleaning action of the instrument. Next the user may begin to follow his own preferred routine for dental hygiene, e.g., alternating the combination usage of brush and fluid jet with usage of the brush alone, followed by removal of the brush and usage of the fluid jet alone.

Typically, the user brushes his teeth to remove particles and plaque from dental surfaces. At his discretion, he may then employ the fluid jet to enhance the brushing action causing more debris and plaque to be removed and carried away from the teeth.

The brushing action, in addition to its cleansing function, performs an important stimulating activity. This massaging of the gums promotes healthy gingival tissue which is vital to proper oral hygiene.

After brushing alone or combined with the fluid jet, is concluded, the user may simply remove the brushing means 10 from fluid jet means 20, so that he may properly irrigate the gingival and sub-gingival areas to completely cleanse the oral periodontal apparatus.

Removal is accomplished simply by pushing the shank 9 of the brushing means 10 away from fluid jet means 20, thereby "un-snapping" the two members.

In this manner, the user may conveniently utilize the best features of both brushing and irrigating in an efficient and sanitary manner.

Figure 4:
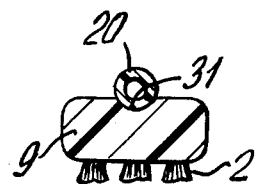
FIG. 4 is a cross-sectional view of the embodiment of FIG. 3, along the lines 4—4 of FIG. 3.

The embodiment of FIGS. 3 and 4 is similar to operation and structure to the embodiment of FIGS. 1 and 2. However, the brushing means 30 of FIGS. 3 and 4 includes a groove 31 on the top side 11 thereof. The groove 31 is designed to accept the body of fluid jet means 20, and extends from the distal end 9 of the brushing means 10, to opening of conduit 8. By placing the fluid jet element 20, into groove 31 the instrument may be fabricated in a more narrow configuration and thus fit more readily into the user's mouth. To this end, flange 4' is shorter than flange 4. This narrower embodiment of the invention has the further advantage of bringing the outlet nozzle 23 of jet element 20 into a closer proximate relationship with the bristles 2, and therefore with the surfaces of the teeth. This serves to enhance the salutary effects mentioned above.

It will be appreciated by those skilled in this art that various changes may be made in the configuration of the invention.

What is claimed is:

1. An oral hygiene device adapted to be removably attached to a fluid jet having an elongated nozzle with an orifice inclined relative to a shank of said nozzle, and having a collar at the distal end of said nozzle, said brush comprising:
   a head having bristles extending laterally thereof;
   a handle extending from said head along a central axis thereof;
   a fluid conduit extending through said head and terminating among said bristles, said conduit being angled relative to said head with an inclination corresponding to the inclination of said orifice relative to said shank for receiving said orifice; and
   resilient means secured to said handle and positioned for engagement with said collar to secure said hygiene device to said jet.

2. A device according to claim 1 wherein said resilient means is a flange, said resilient means urging said nozzle into said conduit to secure said hygiene device to said jet.

3. A device according to claim 2 wherein said hygiene device is a tooth brush, and wherein said handle includes a groove therein for mating with said jet.

* * * * *